(12) United States Patent
Higashiura et al.

(10) Patent No.: US 8,536,342 B2
(45) Date of Patent: Sep. 17, 2013

(54) PROCESS FOR PRODUCING THIABENZOAZULENE-PROPIONIC ACID DERIVATIVE

(75) Inventors: Kunihiko Higashiura, Kato (JP); Taizo Ito, Kato (JP); Takashi Ogino, Kato (JP); Taisuke Hasegawa, Kato (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/383,441

(22) PCT Filed: Jul. 26, 2010

(86) PCT No.: PCT/JP2010/062554
§ 371 (c)(1),
(2), (4) Date: Jan. 30, 2012

(87) PCT Pub. No.: WO2011/013632
PCT Pub. Date: Feb. 3, 2011

(65) Prior Publication Data
US 2012/0123127 A1    May 17, 2012

(30) Foreign Application Priority Data

Jul. 28, 2009 (JP) .................. 2009-175768
Aug. 5, 2009 (JP) .................. 2009-182205

(51) Int. Cl.
*C07C 409/00* (2006.01)
*A61K 31/445* (2006.01)

(52) U.S. Cl.
USPC .......................................... 546/202; 514/324

(58) Field of Classification Search
USPC .......................................... 546/202; 514/324
See application file for complete search history.

(56) References Cited

U.S. PATENT DOCUMENTS

| 4,052,412 A | 10/1977 | Bastian |
| 4,072,756 A | 2/1978 | Ebnother et al. |
| 4,137,323 A | 1/1979 | Bastian |
| 2010/0004456 A1 | 1/2010 | Higashiura et al. |

FOREIGN PATENT DOCUMENTS

| CA | 1011739 A | 6/1977 |
| EP | 2 246 778 A1 | 10/2010 |
| JP | A-49-69677 | 7/1974 |
| JP | A-50-18478 | 2/1975 |
| JP | A-50-82052 | 7/1975 |
| WO | WO 2008/038711 A1 | 4/2008 |
| WO | WO 2009/096080 A1 | 8/2009 |

OTHER PUBLICATIONS

Polivka et al., "4H-Benzo [4,5] Cyclohepta [1,2-b] Thiophenes and 9,10-Dihydro Derivatives-Sulfonium Analogues of Pizotifen and Ketotifen; Chirality of Ketotifen; Synthesis of the 2-Bromo Derivative of Ketotifen", *Collect. Czech. Chem. Commun.*, 1989, pp. 2443-2469, vol. 54, No. 9.
Feb. 7, 2012 International Preliminary Report on Patentability issued in PCT/JP2010/062554.
Dec. 19, 2012 Supplementary European Search Report issued in EP 10 80 4378.

*Primary Examiner* — John Mabry
(74) *Attorney, Agent, or Firm* — Oliff & Berridge, PLC

(57) ABSTRACT

Disclosed is a process for producing a thiabenzoazulene-propionic acid derivative which is useful as an active ingredient of an antihistaminic agent or the like. According to the producing process of the present invention, it is possible to produce a thiabenzoazulene-propionic acid derivative where the 2-position of the thiabenzoazulene skeleton is substituted with propionic acid. The thiabenzoazulene propionic-acid derivative thus synthesized has excellent antagonistic action to histamine H1 receptor and low intracerebral transmigration and, therefore, is useful as an active ingredient of the pharmaceutical composition such as an antihistaminic agent.

7 Claims, No Drawings

US 8,536,342 B2

PROCESS FOR PRODUCING THIABENZOAZULENE-PROPIONIC ACID DERIVATIVE

TECHNICAL FIELD

The present invention relates to a process for producing a thiabenzoazulene-propionic acid derivative which is useful as an active ingredient of pharmaceutical compositions such as an antihistaminic agent.

BACKGROUND ART

Histamine is a representative chemical mediator which induces allergic reaction and is released from cells such as mast cells or basophils when an allergenic substance comes into the body. The released histamine binds to a histamine 1-type receptor (H1 receptor) protein and achieves the pharmacological action such as reduction of blood pressure, promotion of vascular permeability, contraction of smooth muscle, dilation of blood vessel or promotion of gland secretion participating in expression of allergic reaction and inflammation. As such, histamine is related to various human diseases and it is possible to prevent or treat allergic disease and inflammation by suppressing its action. Drugs (antihistaminic drugs) which suppress the histamine release or inhibit the histamine binding to a receptor have been abundantly put into the market and used for the diseases such as bronchial asthma, allergic rhinitis, pollinosis, urticaria and atopic dermatitis.

However, the antihistaminic drugs which have been known up to now express undesirable side effects such as sedative action, drowsiness, dizziness, feeling of malaise, anticholinergic thirst, dry feeling of mucosa or visual accommodation disorder. Accordingly, there are restrictions for its use such as prohibition of ingestion before driving a car and that is a cause of its inconvenient use. Therefore, there has been a demand by patients and the medical practice for antihistaminic agent wherein such a problem is solved and an excellent effect is available. The present inventors have found an excellent synthetic method for a thiabenzoazulene-propionic acid having less central side effect and a potent antihistaminic action whereupon the present invention has been achieved.

With regard to piperidine derivatives having a thiabenzoazulene skeleton where the site between the 9- and 10-positions is a double bond, Patent Document 1 discloses a compound having neuroleptic effect and central depressing effect where the 2-position of the thiabenzoazulene skeleton is substituted with methyl, alcohol or alkyl ketone and the 1-position of piperidine is substituted with alkyl. Patent Document 2 discloses a compound having sedative action, sleep promoting action and muscle relaxing action where the 2-position of the same thiabenzoazulene skeleton is substituted with methyl or chlorine and the 1-position of piperidine is substituted with alkyl ketone. However, there has been no report concerning a synthetic method for a compound where propionic acid is bound to the 2-position of a thiabenzoazulene skeleton which is able to be synthesized by a producing process of the present invention.

PRIOR ART DOCUMENTS

Patent Documents

Patent Document 1: Gazette of Japanese Patent Laid-Open No. Sho-49/069,677A
Patent Document 2: Gazette of Japanese Patent Laid-Open No. Sho-50/018,478A Since it was synthetically difficult to substitute the 3-position of propionic acid with a thiabenzoazulene skeleton in a position-selective manner, a compound where ethoxycarbonylvinyl is introduced into the 2-position of a thiabenzoazulene skeleton [$R_2$ in the formula (I) is ethyl] was synthesized. Since a protective group such as ethoxycarbonyl was previously introduced into the 1-position [$R_1$ of the formula (I)] of a piperidine ring at that time, a commonly used treatment with hydrogen bromide (HBr)-acetic acid was conducted for a purpose of deprotection of the synthesized compound. However, it was found that a double bond of the vinyl moiety in the side chain at the 2-position of the thiabenzoazulene skeleton was transferred to a seven-membered ring moiety (between the 9- and 10-positions) of the thiabenzoazulene skeleton together with the aimed deprotection. As a result of this transfer reaction, a compound where the 2-position of a thiabenzoazulene skeleton is substituted with propionic acid (i.e., 3-[4-piperidin-4-ylidene-4H-1-thiabenzo[f]azulen-2-yl]-propionic acid [$R_1'$ and $R_2'$ in the formula (II) are hydrogens]) was able to be produced for the first time. Since this compound has an excellent antihistaminic action and also has a low intracerebral transmigration, it has very high utility as an active ingredient for a pharmaceutical composition such as an antihistaminic agent having little central side effect such as drowsiness.

SUMMARY OF THE INVENTION

Problems that the Invention is to Solve

An object of the present invention is to provide a process for producing a thiabenzoazulene-propionic acid derivative which is useful as an active ingredient for a pharmaceutical composition such as an antihistaminic agent.

Means for Solving the Problems

No compound where the 2-position of a thiabenzoazulene skeleton whose site between the 9- and 10-positions is a double bond is substituted with propionic acid has been synthesized yet. The producing process of the present invention is based on a new synthetic method in which a compound [formula (I)] where a substituent such as carboxyvinyl or ethoxycarbonylvinyl is introduced into the 2-position of a thiabenzoazulene skeleton is treated with hydrogen bromide-acetic acid or the like whereupon a double bond in the vinyl moiety of the side chain substituent is transferred to the seven-membered ring moiety (between the 9- and 10-positions) of a thiabenzoazulene skeleton. As a result of this transfer reaction, a thiabenzoazulene-propionic acid derivative which is a compound wherein the 2-position of a thiabenzoazulene skeleton is substituted with propionic acid has now been able to be produced.

Advantages of the Invention

The synthesized thiabenzoazulene-propionic acid derivative had an excellent antagonistic action to histamine H1 receptor. Furthermore, it showed a low intracerebral transmigration in an intracerebral receptor binding test by oral administration to mice whereby a reducing effect for the central side effect such as drowsiness was achieved. Accordingly, there is very high utility in the producing process according to the present invention where a thiabenzoazulene-propionic acid derivative having a desirable property as an active ingredient for a pharmaceutical composition such as an antihistaminic agent is able to be synthesized.

MODE FOR CARRYING OUT THE INVENTION

The present invention relates to a process for producing a compound represented by the following formula (II), characterized in that, a compound represented by the following formula (I) is made to react with hydrogen bromide, hydrogen chloride, boron trifluoride, methanesulfonic acid or thionyl chloride in a solvent which is formic acid, acetic acid or propionic acid.

[chem. 1]

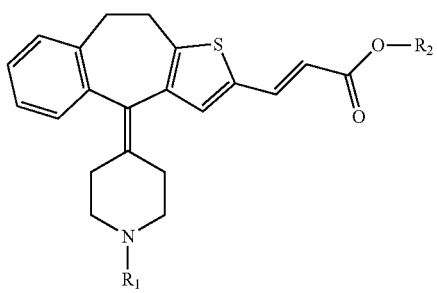

(I)

[chem. 2]

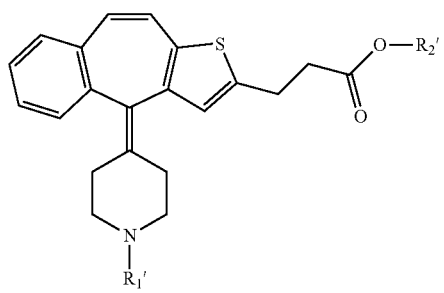

(II)

[In the formulae, $R_1$ and $R_1'$ are same or different and each is hydrogen or COOX where X is alkyl or optionally substituted benzyl or phenyl; and $R_2$ and $R_2'$ are same or different and each is hydrogen, alkyl, diphenylmethyl or optionally substituted benzyl or phenyl.]

In the above formulae (I) and (II), examples of the substituent in "optionally substituted" include halogen, alkyl, alkoxy, nitro and phenyl and said substituent is not limited to just one but may be more than one.

In the formulae (I) and (II), alkyl (including alkyl referred to in the above substituent) is preferably a linear or branched alkyl group having 1 to 6 carbon(s) such as methyl, ethyl, propyl, isopropyl, butyl, isobutyl, sec-butyl, tert-butyl, pentyl, isopentyl, neopentyl, tert-pentyl, hexyl and isohexyl.

In the above substituent, halogen is fluorine, chlorine, bromine, iodine, etc. Alkoxy is preferably a linear or branched alkoxy having 1 to 6 carbon(s) such as methoxy, ethoxy, n-propoxy, isopropoxy, n-butoxy, isobutoxy, sec-butoxy, tert-butoxy, n-pentyloxy and n-hexyloxy.

In the above reaction, a 3-(9,10-dihydro-4H-1-thiabenzo[f]azulen-2-yl)acrylic acid derivative represented by the formula (I) is made to act with a quantity acidic reagent equal or more to said derivative, for example, hydrogen chloride, hydrogen bromide, hydrogen iodide, boron trifluoride, methanesulfonic acid and thionyl chloride, in a solvent such as acetic acid, formic acid or propionic acid at an appropriate temperature preferably between room temperature and boiling point of the solvent. As a result of this reaction, double bond in the acrylic acid moiety is transferred into the ring due to the action of the above acid to said derivative whereupon a 3-(4H-1-thiabenzo[f]-azulen-2-yl)propionic acid derivative represented by the formula (II) is able to be produced. The reaction is able to be carried out for several tens minutes to several hours and, in the case of hydrogen bromide-acetic acid for example, the transfer reaction of the double bond finishes within about 30 minutes at 90 to 100° C. or within about 3 hours at 50 to 55° C.

When $R_1$ in the above formula (I) is a protective group such as ethoxycarbonyl, it is able to be detached by an alkali treatment before the above transfer reaction of the double bond. When the treatment is conducted by an acid, a transfer reaction of the double bond also takes place together with the detachment of the protective group. Since it takes long time for the detachment reaction of the protective group as compared with the transfer reaction of the double bond, the reaction for longer time than the time required for the transfer reaction of the double bond is necessary when both reactions are simultaneously conducted. It is also possible that a tert-butoxycarbonyl group (Boc group) is introduced into $R_1'$ of the formula (II) after the transfer reaction of the double bond (Refer to Example 7 and Example 10). As a result of introduction of a Boc group, lipid solubility is able to be enhanced so that the purification with an organic solvent is made easier. The Boc group is able to be detached by treating with an acid or an alkali according to the conventional detachment reaction.

In using as an active ingredient for drugs, etc., a purified product with very high purity is demanded. For such a purpose, 3-(4-piperidin-4-ylidene-4-H1-thiazo[f]azulen-2-yl) propionic acid synthesized by the producing process of the present invention is converted to a salt whereby its purity is able to be enhanced. For example, it is able to be converted to a salt with an organic sulfonic acid (alkylsulfonic acid such as methanesulfonic acid or ethanesulfonic acid; aromatic sulfonic acid such as p-toluenesulfonic acid, benzenesulfonic acid or naphthalenesulfonic acid; camphor-sulfonic acid; trifluoromethanesulfonic acid; etc.), trifluoroacetic acid, hydrobromic acid, hydroiodic acid, perchloric acid, hydrochloric acid, sulfuric acid, nitric acid or the like. Further, a high purity is able to be achieved according to a recrystallization method. The solvent in converting to a salt and the solvent in the recrystallization method are able to be appropriately selected.

The compounds represented by the above formulae (I) and (II) may include various salts thereof and there may be exemplified acid addition salts with an acid such as hydrochloric acid, oxalic acid, fumaric acid, p-toluenesulfonic acid, maleic acid, succinic acid, acetic acid, citric acid, tartaric acid, carbonic acid or nitric acid. Further, a salt of carboxyl group may also include an appropriate salt with alkali metal or alkali earth metal such as sodium, potassium or calcium. The salt as such is able to be produced from each of the free compounds or is able to be converted each other.

EXAMPLES

The present invention will now be specifically illustrated by way of the following Examples although the present invention is not limited thereto at all.

Melting point was measured by a device for measuring the melting point (Yamato MP-21) after placing a sample in a glass capillary (Correction of a thermometer was not done). MS spectra were measured by POLARIS Q (Thermo Quest).

$^1$H-NMR was measured by a nuclear magnetic resonance device of Bruker ARX500 and chemical shift values were expressed in terms of ppm based on TMS (δ=0 ppm) added thereto as an internal standard. Silica gel column chromatography was conducted using silica gel BW127ZH (Fuji Silicia Kagaku) for chromatography. With regard to thin-layer chromatography, Silica gel F254 (Merck, No. 5715) was used and the detection was conducted using UV lamp and a 5% phosphomolybdic acid coloring reagent in ethanol.

Example 1

Production of ethyl 4-(9,10-dihydro-1-thiabenzo[f]-azulen-4-ylidene)piperidine-1-carboxylate (Compound 1)

A solution of commercially available 4-(9,10-dihydro-1-thiabenzo[f]azulen-4-ylidene)-1-methylpiperidine (200 g) and triethylamine (30 mL) in toluene (1.5 L) was heated at 60° C. and then ethyl chlorocarbonate (162 mL) was gradually dropped into the above solution. In this reaction, vigorous reaction happens in its initial stage and, therefore, careful attention is needed. After finishing the dropping, the mixture was heated to reflux for one hour more. After being allowed to cool, it was washed with a saturated aqueous solution of ammonium chloride, the organic layer was then passed through a short column of silica gel and the product was eluted with 2 L of 5% solution of ethyl acetate in toluene. The solvent was evaporated in vacuo and petroleum ether was added to the residue to crystallize. The crystals were filtered and dried to give 215 g (9%) of the compound 1.

Mp. 110-113° C. MS (EI): m/z 353 [M+]. $^1$HNMR (DMSO-$d_6$) δ: 1.18 (t, J=7.1 Hz, 3H), 2.13-2.16 (m, 1H), 2.18-2.23 (m, 1H), 2.43-2.46 (m, 2H), 2.80-2.83 (m, 2H), 3.03-3.12 (m, 1H), 3.17-3.28 (m, 3H), 3.57-3.62 (m, 1H), 3.69-3.71 (m, 1H), 4.04 (q, J=7.1 Hz, 2H), 6.79 (d, J=5.2 Hz, 1H), 7.01-7.03 (m, 1H), 7.17-7.21 (m, 2H), 7.29-7.31 (m, 2H).

Example 2

Production of ethyl 4-(2-formyl-9,10-dihydro-1-thiabenzo[f]azulen-4-ylidene)piperidine-1-carboxylate (Compound 2)

A mixture of 1,2-dichloroethane (20 mL) and DMF (4.1 mL) was cooled on an ice bath and phosphorus oxychloride (3.5 mL) was dropped thereinto for more than 0.5 hour wherein the liquid temperature was kept within a range of 0 to 5° C. The resulting mixture was stirred at room temperature for one hour more and a solution of the compound 1 (10.6 g) in 1,2-dichloroethane (40 mL) was dropped thereinto during 1 hour. The reaction mixture was stirred at 50° C. for 36 hours and poured into an aqueous solution (200 mL) of potassium carbonate (25 g). The mixture was stirred at room temperature for 1 hour and an organic layer was separated. An aqueous layer was extracted with methylene chloride (3×50 mL), combined with the previously-separated organic layer, washed with water (50 mL) and a saturated saline (50 mL) and dried over anhydrous sodium sulfate. The oily residue prepared by evaporating the solvent in vacuo was dissolved in methyl tertbutyl ether (100 mL). When n-heptane (400 mL) was gradually dropped into this solution, solid began to be deposited whereby the mixture was allowed to stand for 30 minutes. n-Heptane (400 mL) was further added thereto, the mixture was concentrated in vacuo until the solvent became about 200 mL and the resulting crystals were filtered and washed with n-heptane (2×30 mL). The crystals were dried in vacuo at 60° C. for 1 hour to give 8.4 g (73%) of the compound 2.

Mp. 146-149° C. MS (EI): m/z 381 [M+]. $^1$HNMR (DMSO-$d_6$) δ: 1.18 (t, J=7.1 Hz, 3H), 2.15-2.17 (m, 1H), 2.26-2.29 (m, 1H), 2.45-2.51 (m, 1H), 2.81-2.91 (m, 2H), 3.02-3.14 (m, 1H), 3.16-3.43 (m, 3H), 3.60-3.62 (m, 1H), 3.72-3.75 (m, 1H), 4.04 (q, J=7.1 Hz, 2H), 7.06-7.07 (m, 1H), 7.19-7.24 (m, 2H), 7.32-7.34 (m, 1H), 7.76 (s, 1H), 9.82 (s, 1H).

Example 3

Production of 3-[4-(1-ethoxycarbonylpiperidin-4-ylidene)-9,10-dihydro-4H-1-thiabenzo[f]azulen-2-yl] acrylic acid (Compound 3)

To the compound 2 (100 g) were added pyridine (60 mL), piperidine (1 mL) and malonic acid (32.4 g) followed by heating to reflux for one night. After the mixture was allowed to cool, the reaction mixture was added to 2 mol/L hydrochloric acid (740 mL), the solidified product was well crushed and then crystals were filtered. The crystals were washed with water (1 L) and dried in vacuo to give 111 g (100%) of the compound 3.

Mp. 228° C. (dec.). $^1$H-NMR (DMSO-$d_6$) δ: 1.18 (t, J=7.0 Hz, 3H), 2.08-2.14 (m, 1H), 2.43-2.48 (m, 1H), 2.49-2.53 (m, 2H), 2.81-2.83 (m, 2H), 3.01-3.15 (m, 1H), 3.22-3.29 (m, 3H), 3.57-3.59 (m, 1H), 3.70-3.72 (m, 1H), 4.05 (q, J=7.0 Hz, 2H), 6.00 (d, J=15.7 Hz, 1H), 7.02-7.04 (m, 1H), 7.17-7.23 (m, 3H), 7.30-7.32 (m, 1H), 7.65 (d, J=15.7 Hz, 1H).

Example 4

Production of 3-(4-piperidin-4-ylidene-9,10-dihydro-4H-1-thiabenzo[f]azulen-2-yl)acrylic acid (Compound 4)

The compound 3 (42.4 g) and potassium hydroxide (66 g) were added to isopropyl alcohol (500 mL) followed by heating to reflux for 24 hours. After the mixture was allowed to cool, the solvent was evaporated in vacuo to an extent of one half by volume and water (500 mL) was added to the residue. The mixture was cooled with ice and its pH was adjusted to 7 using 2 mol/L hydrochloric acid. The solid deposited therefrom was filtered, washed with a sufficient amount of water and dried in vacuo at 50° C. to give 35.8 g (85%) of the compound 4.

Mp. 269-272° C. (dec.). MS (EI): m/z 351 [M$^+$]. $^1$H-NMR (DMSO-$d_6$+trifluoroacetic acid (5%)) δ: 2.32-2.39 (m, 1H), 2.45-2.50 (m, 1H), 2.60-2.67 (m, 1H), 2.70-2.76 (m, 1H), 2.81-2.90 (m, 2H), 2.92-3.00 (m, 1H), 3.05-3.13 (m, 1H), 3.18-3.25 (m, 1H), 3.28-3.38 (m, 3H), 6.02 (d, J=15.7 Hz, 1H), 7.06-7.10 (m, 1H), 7.18-7.26 (m, 2H), 7.27 (s, 1H), 7.32-7.36 (m, 1H), 7.68 (d, J=15.7 Hz, 1H), 8.68-8.84 (br, 2H).

Example 5

Production of 3-(4-piperidin-4-ylidene-4H-1-thiabenzo-[f]azulen-2-yl)propionic acid (Compound 5)

(1) After 30% HBr solution in acetic acid (80 mL) was added to a mixture of the compound 4 (40 g) and acetic acid (800 mL), the mixture was stirred at 55 to 60° C. for 3 hours. After the mixture was allowed to cool, the solvent was evaporated in vacuo, 1 mol/mL aqueous solution (400 mL) of sodium hydroxide was added to the residue, the mixture was heated at 40 to 50° C. and dissolved by addition of ethanol (200 mL) thereto. After the pH was adjusted to 7-8 by addition of an appropriate amount of 1 mol/L hydrochloric acid thereto together with continuing the heating at 40 to 50° C., the mixture was stirred at room temperature for 16 hours. After ethanol was evaporated in vacuo, the solid deposited therefrom was filtered and washed with water (2×100 mL) and ethanol (2×100 mL). The resulting solid was dried in vacuo at 60° C. for 16 hours to give 32 g (80%) of crude crystals of the compound 5 where a double bond of acrylic acid binding to a thiophene ring was transferred to a seven-membered ring moiety. As a result of HPLC analysis, its purity was 87%.

(2) The above operation (1) is a process for producing the compound 5 where a double bond of acrylic acid binding to a thiophene ring was transferred to a seven-membered ring moiety by such a manner that the compound 3 is subjected to an alkali treatment to detach the ethoxycarbonyl group and the resulting compound 4 is subjected to a treatment with HBr-acetic acid. It is also possible to produce the compound 5 by another process where the compound 3 is directly subjected to a treatment with HBr-acetic acid whereupon a transfer reaction of the double bond is done together with the reaction of detaching the ethoxycarbonyl group.

(3) The crude crystals (5 g) of the compound 5 prepared in the above operation (1) were added to 1.8 mol/L aqueous solution (35 mL) of sodium hydroxide followed by heating to reflux to give a homogeneous solution. This was gradually cooled down to room temperature for more than 1.5 hours and the solid deposited therefrom was filtered and washed with 1.8 mol/L aqueous solution (2×5 mL) of sodium hydroxide and methylene chloride (2×5 mL). The resulting solid was added to water (100 mL) followed by heating to reflux to give an almost homogeneous solution. To this solution was added 1 mol/L hydrochloric acid at 90 to 100° C. so that the pH was adjusted to 7-8. After this was allowed to cool down to room temperature, the resulting crystals were filtered and washed with water (2×5 mL) and ethanol (2×5 mL). The resulting crystals were added to ethanol (100 mL) followed by heating to reflux for 1 hour. After this was allowed to cool, the crystals were filtered, washed with ethanol (2×5 mL) and dried in vacuo at 50 to 60° C. for 4 hours to give 2.6 g (recovery rate: 52%) of the compound 5 in 99.6% purity (by HPLC analysis).

Mp. 254° C. (dec.). MS (EI): m/z 351 [M+]. $^1$HNMR (DMSO-$d_6$) δ 1.92-1.99 (m, 1H), 2.14-2.20 (m, 1H), 2.22-2.28 (m, 1H), 2.38-2.44 (m, 1H), 2.49 (t, J=7.2 Hz, 2H), 2.55-2.68 (m, 2H), 2.83-2.94 (m, 2H), 2.97 (t, J=7.2 Hz, 2H), 6.70 (s, 1H), 6.83 (d, J=11.5 Hz, 1H), 6.89 (d, J=11.5 Hz, 1H), 7.09-7.13 (m, 1H), 7.26-7.32 (m 1H), 7.36-7.40 (m, 2H).

Example 6

Production of 3-[4-(1-tert-butoxycarbonylpiperidin-4-ylidene)-9,10-dihydro-4H-1-thiabenzo[f]azulen-2-yl]acrylic acid (Compound 6)

The compound 3 (45.1 g) and potassium hydroxide (66 g) were added to isopropyl alcohol (500 mL) followed by heating to reflux for 8 hours. After it was allowed to cool, water (500 mL) was added to the reaction mixture followed by heating at 60° C. and, after that, a solution of di-tert-butyl dicarbonate (24 g) in isopropyl alcohol (100 mL) was dropped thereinto. After stirring for 4 hours, the reaction solution was allowed to cool to room temperature and the organic solvent was evaporated therefrom in vacuo. Citric acid was added to the residual aqueous solution so that the pH was adjusted to 4-5 and the solid deposited therefrom was filtered and well washed with water. It was then dried in vacuo at 50° C. for 24 hours to give 44.9 g (99%) of the compound 6.

Mp. 186° C. (dec.). $^1$H-NMR (DMSO-$d_6$) δ: 1.40 (s, 9H), 2.08-2.14 (m, 1H), 2.21-2.32 (m, 1H), 2.41-2.53 (m, 2H), 2.79-2.83 (m, 2H), 3.01-3.15 (m, 1H), 3.21-3.29 (m, 3H), 3.51-3.54 (m, 1H), 3.64-3.67 (m, 1H), 6.00 (d, J=15.7 Hz, 1H), 7.02-7.04 (m, 1H), 7.10-7.11 (m, 1H), 7.16-7.23 (m, 2H), 7.30-7.32 (m, 1H), 7.52 (d, J=15.7 Hz, 1H).

Example 7

Production of 3-[4-(1-tert-butoxycarbonylpiperidin-4-ylidene)-4H-1-thiabenzo[f]azulen-2-yl]propionic acid (Compound 7)

(1) The compound 6 (39.0 g) was dissolved in acetic acid (700 mL), 30% HBr solution in acetic acid (162 mL) was added thereto and the mixture was stirred at room temperature for 1 hour. After stirring at 100° C. for another 1 hour, the solvent was evaporated in vacuo to give a residue containing a salt of the compound 5 with HBr where Boc group was detached therefrom and a double bond of acrylic acid bound to a thiophene ring was transferred to a seven-membered ring moiety.

(2) To this residue were added water (200 mL), isopropyl alcohol (400 mL) and 2 mol/L aqueous solution (500 mL) of sodium hydroxide to dissolve and a solution of di-tert-butyl dicarbonate (21.9 g) in isopropyl alcohol (100 mL) was dropped thereinto. After the mixture was stirred at room temperature for 20 hours, the organic solvent was evaporated therefrom in vacuo and the aqueous layer was made acidic using citric acid. After it was extracted with methylene chloride (3×100 mL), the organic layers were combined, washed with water (100 mL) and a saturated saline (100 mL) and dried over anhydrous sodium sulfate. The oily residue prepared by evaporating the solvent in vacuo was purified by silica gel column chromatography (methylene chloride:acetone=19:1) and the resulting oily substance was crystallized from petroleum ether to give 22.5 g (60%) of the compound 7.

Mp. 172° C. (dec.). MS (EI): m/z 451 [M+]. $^1$H-NMR (DMSO-$d_6$) δ: 1.39 (s, 9H), 1.88-1.95 (m, 1H), 2.08-2.15 (m, 1H), 2.19-2.26 (m, 1H), 2.34-2.40 (m, 1H), 2.55-2.61 (m, 2H), 2.99 (t, J=7.2 Hz, 2H), 3.06-3.22 (m, 2H), 3.39-3.51 (m, 2H), 6.73 (s, 1H), 6.84 (d, J=11.5 Hz, 1H), 6.90 (d, J=11.5 Hz, 1H), 7.12-7.16 (m, 1H), 7.27-7.32 (m, 1H), 7.36-7.42 (m, 2H).

Example 8

Production of 3-(4-piperidin-4-ylidene-4H-1-thiabenzo-[f]azulen-2-yl)propionic acid (Compound 5)

The compound 7 (13.5 mmol) was added to formic acid (210 mL) followed by stirring at room temperature for 2 hours. After evaporation of the solvent in vacuo, water was added to the residue and the solvent was evaporated again in vacuo. This operation was repeated for three times and the white crystals deposited therefrom was filtered after adding ethanol (100 mL) thereto and washed with ethanol (50 mL) to give 9.71 g (92%) of the compound 5.

Example 9

Production of ethyl 4-[2-(2-ethoxycarbonylvinyl)-9,10-dihydro-1-thiabenzo[f]azulen-4-ylidene]piperidine-1-carboxylate (Compound 8)

Sodium hydride (60% in mineral oil) (3.6 g) was added to 500 mL round-bottom flask under an argon atmosphere and washed with n-hexane (3×30 mL). After n-hexane was removed in vacuo, anhydrous THF (90 mL) was added thereto under an argon atmosphere. A solution of ethyl diethylphosphonoacetate (18 mL) in anhydrous THF (30 mL) was dropped into the above mixture during 30 minutes under cooling with ice followed by stirring at room temperature for another 30 minutes. A solution of the compound 2 (31.2 g) in THF (200 mL) was dropped thereinto at room temperature during 1 hour followed by stirring for another 1 hour. After the reaction mixture was poured into ice water (500 mL), an organic layer was separated therefrom and an aqueous layer was extracted with ethyl acetate (3×100 mL). The organic layers were combined, washed with water (2×100 mL) and a saturated saline (50 mL) and dried over anhydrous sodium sulfate. The solvent was evaporated in vacuo and the resulting oily residue was recrystallized from petroleum ether to give 29.7 g (81%) of the compound 8 in white crystals.

Mp. 90-93° C. MS (EI): m/z 451 [M+]. $^1$H-NMR (DMSO-d$_6$) δ: 1.18 (t, J=7.0 Hz, 3H), 1.22 (t, J=7.1 Hz, 3H), 2.08-2.14 (m, 1H), 2.43-2.48 (m, 1H), 2.49-2.53 (m, 2H), 2.81-2.83 (m, 2H), 3.01-3.15 (m, 1H), 3.22-3.29 (m, 3H), 3.57-3.59 (m, 1H), 3.70-3.72 (m, 1H), 4.05 (q, J=7.0 Hz, 2H), 4.16 (q, J=7.1 Hz, 2H), 6.07 (d, J=15.7 Hz, 1H), 7.01-7.04 (m, 1H), 7.17-7.23 (m, 2H), 7.28 (s, 1H), 7.30-7.32 (m, 2H), 7.71 (d, J=15.7 Hz, 1H).

Example 10

Production of ethyl 3-[4-(1-tert-butoxy-carbonylpiperidin-4-ylidene)-4H-1-thiabenzo[f]azulen-2-yl]-propionate (Compound 10)

(1) A mixture of the compound 8 (9.0 g), acetic acid (200 mL) and 30% HBr solution in acetic acid (19 mL) was heated to reflux for 6 hours. The solvent was evaporated in vacuo, the resulting oily residue was dissolved in water (100 mL) and potassium carbonate (20 g) was added to give ethyl 3-(4-piperidin-4-ylidene)-4H-1-thiabenzo[f]azulen-2-yl]-propionate where an ethoxycarbonyl group was detached therefrom and, at the same time, a double bond bound of acrylic acid to a thiophene ring was transferred to a seven-membered ring moiety.

(2) Without isolating the compound 9 from the above, a solution of di-tert-butyl dicarbonate (4.4 g) in acetonitrile (100 mL) was dropped thereinto at room temperature. After stirring at room temperature for 20 hours, the reaction mixture was added to water (100 mL) followed by extracting with ethyl acetate (3×50 mL). The organic layers were combined, washed with water (100 mL) and a saturated saline (50 mL) and dried over anhydrous sodium sulfate. The oily residue obtained by evaporating the solvent in vacuo was purified by silica gel column chromatography (hexane:ethyl acetate=9:1) to give 5.3 g (55%) of the compound 10 as an oily product.

MS (EI): m/z 479 [M+]. $^1$H-NMR (DMSO-d$_6$) δ: 1.16 (t, J=7.1 Hz, 3H), 1.39 (s, 9H), 1.88-1.96 (m, 1H), 2.08-2.15 (m, 1H), 2.19-2.26 (m, 1H), 2.33-2.40 (m, 1H), 2.59-2.72 (m, 2H), 3.03 (t, J=7.2 Hz, 2H), 3.06-3.19 (m, 2H), 3.39-3.51 (m, 2H), 4.05 (q, J=7.1 Hz, 2H), 6.73 (s, 1H), 6.84 (d, J=11.5 Hz, 1H), 6.90 (d, J=11.5 Hz, 1H), 7.11-7.16 (m, 1H), 7.27-7.33 (m, 1H), 7.37-7.42 (m, 2H).

Example 11

Production of 3-[4-(1-tert-butoxycarbonylpiperidin-4-ylidene)-4H-1-thiabenzo[f]azulen-2-yl]propionic acid (Compound 7)

To a solution of the compound 10 (5.3 g) in ethanol (100 mL) was added 2 mol/L aqueous solution (11 mL) of sodium hydroxide followed by stirring for 20 hours. After evaporating the solvent in vacuo, the residue was dissolved in water (50 mL) and citric acid (10 g) was added thereto followed by extracting with ethyl acetate (3×50 mL). The organic layers were combined, washed with water (50 mL) and a saturated saline (50 mL) and dried over anhydrous sodium sulfate. The oily residue obtained by evaporation of the solvent was crystallized from petroleum ether to give 3.7 g (74%) of the compound 7. The compound 7 was treated in the same manner as in Example 8 to give the compound 5.

Example 12

Production of 4-(2-bromo-9,10-dihydro-1-thiabenzo[f]-azulen-4-ylidene)-1-methylpiperidine (Compound 11)

Bromine (1.0 mL) was dropped into a solution of 4-(9,10-dihydro-1-thiabenzo[f]azulen-4-ylidene)-1-methylpiperidine (5.76 g) in chloroform (50 mL) at 0° C. After the mixture was stirred at room temperature for 2 hours, a saturated aqueous solution of sodium bicarbonate was added thereto and an organic layer was separated therefrom. The organic layer was washed with a saturated saline and dried over anhydrous sodium sulfate. The solvent was evaporated in vacuo and the residue was purified by column chromatograph (chloroform:methanol=9:1) to give 5.6 g (91%) of the compound 11 in white crystals.

Mp. 141-142° C. MS (EI): m/z 375 [M$^+$+2], 373 [M$^+$]. $^1$H-NMR (DMSO-d$_6$) δ: 1.90-2.79 (m, 13H), 3.18-3.22 (m, 2H), 6.85 (s, 1H), 6.98-7.30 (m, 4H).

Example 13

Production of ethyl 4-(2-bromo-9,10-dihydro-1-thiabenzo[f]azulen-4-ylidene)piperidine-1-carboxylate (Compound 12)

Ethyl chlorocarbonate (32 mL) was added to a solution of the compound 11 (21.0 g) in toluene (200 mL) followed by heating to reflux for 6 hours. After allowing it to cool, the reaction mixture was added to a saturated aqueous solution of sodium bicarbonate to separate an organic layer. The organic layer was washed with a saturated saline and dried over anhydrous sodium sulfate, the solvent was evaporated therefrom in vacuo and the residue was purified by column chromatography (hexane:ethyl acetate=19:1) to give 15.0 g (62%) of the compound 12 as an oily product.

MS (EI): m/z 433 [M$^+$+2], 431 [M$^+$]. $^1$H-NMR (DMSO-d$_6$) δ: 1.17 (t, J=7.1 Hz, 3H), 2.10-2.23 (m, 2H), 2.38-2.48 (m, 2H), 2.68-2.83 (m, 2H), 2.92-3.26 (m, 4H), 3.52-3.78 (m, 2H), 4.04 (q, J=7.1 Hz, 2H), 6.90 (s, 1H), 7.02-7.13 (m, 1H), 7.16-7.36 (m, 3H).

Example 14

Production of ethyl 4-(2-bromo-9,10-dihydro-1-thiabenzo[f]azulen-4-ylidene)piperidine-1-carboxylate (Compound 12)

Bromine (10.9 mL) was dropped into a solution of the compound 1 (50 g) in chloroform (500 mL) at room temperature followed by stirring for 2 hours. The reaction mixture was washed with an aqueous solution (100 mL) of sodium thiosulfate and a saturated aqueous solution (100 mL) of potassium carbonate successively and an organic layer was dried over anhydrous sodium sulfate. The solvent was evaporated in vacuo and the residue was purified by silica gel column chromatography (hexane:ethyl acetate=9:1) to give 6.7 g (100%) of the compound 12.

Example 15

Production of ethyl 4-[2-(2-ethoxycarbonylvinyl)-9, 10-dihydro-1-thiabenzo[f]azulen-4-ylidene]piperidine-1-carboxylate (Compound 8)

Ethyl acrylate (18.5 mL), triethylamine (24 mL), palladium acetate (0.3 g) and tri(o-toluyl)phosphine (2.0 g) were added to a solution of the compound 12 (8.80 g) in DMF (50 mL) under an argon stream followed by stirring for one night at 80° C. After allowing it to cool, water was added to the reaction mixture followed by extracting with ethyl acetate and the organic layer was washed with a saturated saline and dried over anhydrous sodium sulfate. The solvent was evaporated therefrom in vacuo and the residue was purified by column chromatography (hexane:ethyl acetate 9:1) to give 6.1 g (79%) of the compound 8.

Example 16

Production of 3-(4-piperidin-4-ylidene-4H-1-thia-benzo-[f]azulen-2-yl)propionic acid (Compound 5)

30% HBr solution in acetic acid (3.8 mL) was added to a solution of the compound 8 (6.10 g) in acetic acid (50 mL) followed by stirring at 120° C. for 4 hours and the reaction product was allowed to cool down to room temperature. As a result of analysis of the reaction product, it was confirmed that the compound 9 where ethoxycarbonyl group was detached and the double bond of the acrylic acid moiety bound to a thiophene ring was transferred to the seven-membered ring moiety was produced. After that, the residue obtained by evaporation of the solvent in vacuo was dissolved in ethanol (50 mL) and 2 mol/L aqueous solution of sodium hydroxide (14 mL) was added thereto followed by stirring at room temperature for 3 hours. After evaporating the solvent, water was added to the residue and the resulting aqueous solution was adjusted to pH 7 using diluted hydrochloric acid followed by extracting with chloroform to give the compound 5.

Example 17

Production and recrystallization of p-toluene-sulfonate of 3-(4-piperidin-4-ylidene)-4H-1-thia-benzo[f]azulen-2-yl) propionic acid (Compound 5)

(1) The compound 5 (4.0 g; purity: 96.9%) was dispersed in acetone (120 mL) and then p-toluenesulfonate monohydrate (2.16 g) was added thereto at room temperature. After stirring for 1 hour, the crystals deposited therefrom were filtered and washed with acetone (20 mL) to give 4.5 g (yield: 75%) of p-toluenesulfonate of the compound 5 in 99.1% purity.

(2) The above product (1.0 g) was added to a mixed solvent (13 mL) of water, isopropyl alcohol and cyclopentyl methyl ether (3:37:60), completely dissolved by heating to reflux and allowed to cool down to room temperature and the crystals deposited therefrom were filtered and washed with the previously-mentioned mixed solvent (5 mL) to give 0.68 g (recovery rate: 68%) of 3-(4-piperidin-4-ylidene)-4H-1-thia-benzo [f]azulen-2-yl)propionic acid p-toluenesulfonate in 99.8% purity.

Example 18

Production and recrystallization of benzenesulfonate of 3-(4-piperidin-4-ylidene-4H-1-thiabenzo[f]azu-len-2-yl) propionic acid (Compound 5)

(1) The compound 5 (4.0 g; purity: 96.9%) was dispersed in acetone (120 mL) and benzenesulfonic acid monohydrate (2.02 g) was added thereto at room temperature. After stirring for 15 hours, the crystals deposited therefrom were filtered and washed with acetone (20 mL) to give 2.7 g (yield: 46%) of benzenesulfonate of the compound 5 in 99.9% purity.

(2) 3-(4-Piperidin-4-ylidene-4H-1-thiabenzo[f]azulen-2-yl-propionic acid benzenesulfonate of 99.6% purity (1.0 g) was dissolved in acetone (50 mL) by heating and allowed to cool down to room temperature and the crystals deposited therefrom were filtered to give 0.30 g (recovery rate: 30%) of 3-(4-piperidin-4-ylidene-4H-1-thiabenzo[f]azulen-2-yl) propionic acid benzenesulfonate of 100% purity.

Example 19

Production and recrystallization of methanesulfonate of 3-(4-piperidin-4-ylidene-4H-1-thiabenzo[f]azu-len-2-yl)-propionic acid (Compound 5)

The compound 5 (0.5 g; purity: 96.9%) was dispersed in acetone (10 mL) and methanesulfonic acid (0.14 g) was added thereto at room temperature. After stirring for 40 hours, the crystals deposited therefrom were filtered and washed with acetone (2 mL) to give 0.49 g (yield: 77%) of methanesulfonate of the compound 5 in 98.7% purity.

Example 20

Production of hydrochloride, sulfate and nitrate of 3-(4-piperidin-4-ylidene-4H-1-thiabenzo[f]azulen-2-yl)-propionic acid (Compound 5)

(1) The compound 5 (0.5 g; purity: 96.9%) was dispersed in acetone (10 mL) and 2 mol/L hydrochloric acid (0.9 mL) was added thereto at room temperature. After stirring for 1 hour, the crystals deposited therefrom were filtered and washed with acetone (2 mL) to give 0.39 g (yield: 71%) of hydrochloride of the compound 5 in 98.2% purity.

(2) The compound 5 (4.0 g; purity: 96.9%) was dissolved in formic acid (80 mL) and concentrated sulfuric acid (1.13 g) was added thereto under cooling with ice. After stirring for 1 hour, the solvent was evaporated therefrom in vacuo, water (40 mL) was added to the resulting residue and the crystals deposited therefrom were filtered and washed with cold water (2 mL) to give 0.39 g (yield: 76%) of sulfate of the compound 5 in 97.4% purity.

(3) The compound 5 (0.5 g; purity: 96.9%) was dispersed in water (40 mL) and 70% nitric acid (0.2 mL) was added thereto under cooling with ice. After stirring for 1 hour, the crystals deposited therefrom were filtered and washed with water (2 mL) to give 0.39 g (yield: 71%) of nitrate of the compound 5 in 98.4% purity.

Example 21

Production of hydrochloride of 3-(4-piperidin-4-ylidene-4H-1-thiabenzo[f]azulen-2-yl)propionic propionic acid (Compound 5)

The compound 5 (2.85 kg; purity: 99.8%) was dispersed in water (37 kg) heated at 80 to 90° C. and stirred for 30 minutes. To this was added 2 mol/L hydrochloric acid (4.1 kg) followed by stirring at the same temperature for 30 minutes so that the compound 5 was dissolved. The insoluble matter was filtered where the temperature was still maintained and then 2 mol/L hydrochloric acid (2.05 kg) was added to the filtrate. The mixture was cooled down to 10 to 20° C. and stirred for 17 hours. The crystals deposited therefrom were filtered, washed with water (3×2 L) and dried at 60 to 65° C. for 48 hours to give 2.79 kg (yield: 88.7%) of hydrochloride of the compound 5 in 99.91% purity.

INDUSTRIAL APPLICABILITY

In accordance with the producing process of the present invention, a compound [formula (I)] where a substituent such as carboxyvinyl or ethoxycarbonylvinyl group is introduced into the 2-position of a thiabenzoazulene skeleton is treated with hydrogen bromide-acetic acid or the like whereupon it is now possible to produce a compound where the 2-position of the thiabenzoazulene skeleton is substituted with propionic acid on the basis of a novel synthetic method of transferring a double bond in a vinyl moiety of the side chain substituent to a seven-membered ring moiety (between the 9- and 10-positions) of the thiabenzoazulene skeleton. 3-(4-Piperidin-4-ylidene-4H-1-thiabenzo[f]azulen-2-yl) propionic acid (compound 5), etc. synthesized by the producing method of the present invention had an excellent antagonistic action to histamine H1 receptor. Furthermore, they showed a low intracerebral transmigration according to an intracerebral receptor binding test by oral administration to mice whereby they achieved a reducing effect for a central side effect such as drowsiness. Accordingly, the producing process of the present invention which is able to synthesize the above compounds having the desirable property as an active ingredient of the pharmaceutical composition such as an antihistaminic agent has very high utility.

The invention claimed is:

1. A process for producing a compound represented by the following formula (II), comprising reacting a compound represented by the following formula (I) with hydrogen bromide, hydrogen chloride, boron trifluoride, methanesulfonic acid or thionyl chloride in a solvent selected from the group consisting of formic acid, acetic acid and propionic acid:

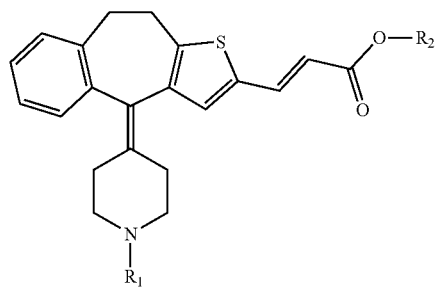

(I)

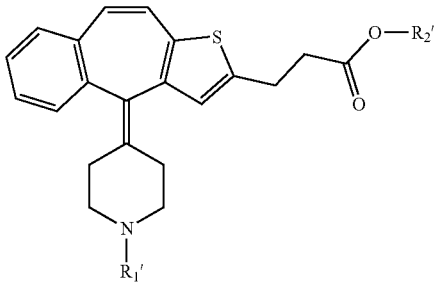

(II)

wherein in the formulae, $R_1$ and $R_1'$ are same or different and each is hydrogen or COOX where X is alkyl or optionally substituted benzyl or phenyl; and $R_2$ and $R_2'$ are same or different and each is hydrogen, alkyl, diphenylmethyl or optionally substituted benzyl or phenyl.

2. The process for producing the compound according to claim 1, wherein both $R_1'$ and $R_2'$ in the formula (II) are hydrogens.

3. The process for producing the compound according to claim 2, wherein the compound where both $R_1$ and $R_2$ in the formula (I) are hydrogens is used.

4. The process for producing the compound according to claim 1, wherein the group of $R_1'$ or $R_2'$ which is a group except hydrogen in a compound of the formula (II) is detached to produce a compound of the formula (II) where both $R_1'$ and $R_2'$ are hydrogens.

5. The process for producing the compound according to claim 1, wherein a compound of the formula (II) where both $R_1'$ and $R_2'$ are hydrogens is further converted to a salt.

6. The process according to claim 5, wherein the salt is an organic sulfonate.

7. The process according to claim 5, wherein the salt is a hydrochloride.

* * * * *